United States Patent [19]

Geprägs et al.

[11] Patent Number: 6,133,410
[45] Date of Patent: Oct. 17, 2000

[54] LINEAR ALTERNATING FUNCTIONALIZED α-OLEFIN/CO-COPOLYMERS AND THEIR USE IN PREPARING ION-SELECTIVE MEMBRANES

[75] Inventors: Michael Geprägs, Lambsheim; Joachim Queisser, Mannheim; Bernhard Rieger, Ulm; Martin Möller, Ulm; Adnan S. Abu-Surrah, Ulm; Harm-Anton Klok, Neu-Ulm; Peter Eibeck, Ulm; Markus Schmid, Pfullingen, all of Germany

[73] Assignee: BASF Aktiengesellschaft, Ludwigshafen, Germany

[21] Appl. No.: 09/402,091

[22] PCT Filed: May 18, 1998

[86] PCT No.: PCT/EP98/01553

§ 371 Date: Sep. 29, 1999

§ 102(e) Date: Sep. 29, 1999

[87] PCT Pub. No.: WO98/45352

PCT Pub. Date: Oct. 15, 1998

[30] Foreign Application Priority Data

Apr. 4, 1997 [DE] Germany ............ 197 14 031

[51] Int. Cl.⁷ ................ C08G 67/02; C08J 3/02
[52] U.S. Cl. .......... 528/392; 528/405; 524/706; 524/709; 524/710; 524/711; 524/841; 524/845; 524/849
[58] Field of Search .................. 528/392, 405; 524/706, 709, 710, 711, 841, 845, 849

[56] References Cited

U.S. PATENT DOCUMENTS 5,241,036 8/1993 Hsiue et al. .
5,352,767 10/1994 Chien .

FOREIGN PATENT DOCUMENTS

| 121 965 | 10/1984 | European Pat. Off. . |
|---|---|---|
| 416 681 | 3/1991 | European Pat. Off. . |
| 501 576 | 9/1992 | European Pat. Off. . |
| 512 647 | 11/1992 | European Pat. Off. . |
| 516 238 | 12/1992 | European Pat. Off. . |
| 562 698 | 9/1993 | European Pat. Off. . |
| 196 10 358 | 9/1997 | Germany . |
| 196 49 072 | 6/1998 | Germany . |
| 98/45352 | 10/1998 | WIPO . |

OTHER PUBLICATIONS

F. Vogtle, Supramolekulare Chemie, B.G. Teubner, 1989, p. 47.
C.J. Pedersen, J. Am. Chem. Soc., 1967, 89, 7017–7036.
Macromolecules 1989, 22, 4408–4412, Percec et al.
Bourgoin et al., J. Am. Chem. Soc. 97:12 Jun. 11, 1975 3462–3467.
Moody et al., Selective Electrode Rev., 1988, 10, 71.
Reinhoudt et al., Anal. Chem, 1994, 66, 3618–3623.
Makromol. Chem. 194, 2579–2603 (1993) Xu et al.
Derwent Abst. JP 5 9135–224.
Vogel's Handbook of Practical Organic Chem. 5, Aufl., 1989.

*Primary Examiner*—Samuel A. Acquah
*Attorney, Agent, or Firm*—Keil & Weinkauf

[57] ABSTRACT

Linear, alternating α-olefin-CO copolymers are obtainable by polymerization of a monomer mixture comprising
  a) carbon monoxide,
  b) 1-alkenes which are functionalized by a covalently bonded crown ether unit or cryptand unit A containing at least 5 heteroatoms selected from the group consisting of nitrogen, oxygen, sulfur and/or selenium in the polyheteroatom framework, and, if desired,
  c) $C_2$–$C_{24}$-1-alkenes.

10 Claims, No Drawings

LINEAR ALTERNATING FUNCTIONALIZED α-OLEFIN/CO-COPOLYMERS AND THEIR USE IN PREPARING ION-SELECTIVE MEMBRANES

The present invention relates to linear, alternating α-olefin-CO copolymers obtainable by polymerization of a monomer mixture comprising a) carbon monoxide, b) 1-alkenes which are functionalized by a covalently bonded crown ether unit or cryptand unit A containing at least heteroatoms selected from the group consisting of nitrogen, oxygen, sulfur and selenium in the polyheteroatom framework, and, if desired, c) $C_2$–$C_{24}$-1-alkenes.

The invention further relates to a process for preparing the functionalized α-olefin-CO copolymers and also to their use for producing moldings, films, fibers and coatings. The invention also relates to ion-selective membranes which can be produced from the functionalized α-olefin-CO copolymers and their use as a constituent of ion-selective electrodes or chemically modified field effect transistors.

Binary and ternary α-olefin-CO copolymers (carbon monoxide copolymers) have been adequately described in the specialized literature. For example, EP-B 121 965 discloses ethene-CO copolymers, EP-A 416 681 discloses ethene-propene-CO copolymers. Carbon monoxide copolymers made up of carbon monoxide and 1-butene or 1-hexene (cf. U.S. Pat. No. 5,352,767) and also carbon monoxide terpolymers with longer-chain α-olefins have already been described (cf. unpublished German Patent Application 19649072.3).

While conventional carbon monoxide-ethene copolymers are hard but brittle and are now used as engineering plastics, carbon monoxide copolymers having high mean molecular weights $M_w$ (above 80,000 g/mol) (cf. the unpublished German Patent Application 196 10 358.4) or carbon monoxide copolymers comprising long-chain α-olefin units (>$C_6$) also make it possible to obtain molding compositions having a thermoplastic, elastomeric property profile, ie. copolymers whose glass transition temperatures ($T_g$) are less than 20° C.

The range of applications of the known carbon monoxide copolymers is kept within narrow limits by the selection of the monomer components which form them.

It would therefore be desirable to be able to incorporate precisely those monomer components which help to eliminate the disadvantages, eg. the brittleness, arising from the carbon monoxide framework and which at the same time offer the opportunity of obtaining novel molding compositions which are also suitable for complex special applications by exploiting the properties given by just this basic framework, ie. having hydrophobic behavior and nevertheless being relatively polar.

It is an object of the present invention to find novel carbon monoxide copolymers which, as a result of selection of the monomer components, have a combination of matched properties in the product and are therefore suitable for complex applications. In particular, it is an object of the invention to provide ion-selective membranes which consist essentially of the carbon monoxide copolymers of the present invention or have these as essential constituents and which do not have the indicated disadvantages of such membranes or membrane systems.

We have found that this object is achieved by means of the carbon monoxide copolymers described in the introduction. Furthermore, we have found a process for preparing the carbon monoxide copolymers of the present invention and their use for the production of fibers, moldings, coatings, films and ion-selective membranes. We have also found ion-selective membranes based on the carbon monoxide copolymers of the present invention and their use as constituents of ion-selective electrodes or chemically modified field effect transistors.

Preference is given to α-olefin-CO copolymers which can be prepared by copolymerization of the components a) carbon monoxide, b) a 1-alkene which is functionalized by a covalently bonded crown ether unit A containing from 5 to 10 oxygen atoms, and c) a $C_2$–$C_{24}$-1-alkene.

Particular preference is given to α-olefin-CO copolymers which are obtainable by copolymerization of carbon monoxide (a)), a functionalized 1-alkene (b)) of the formula (I)

where

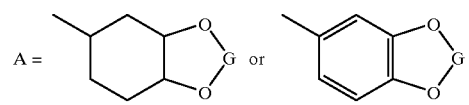

where

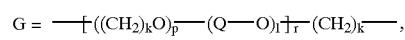

where the substituents and indices have the following meanings:

Q=1,2-cyclohexyl or 1,2-phenyl, k=independently of one another 2, 3 or 4, p=1, 2, 3 or 4, l=0 or 1, r=1, 2, 3 or 4 and q=an integer in the range from 4 to 24, in particular in the range from 6 to 16, and a $C_3$–$C_{18}$-1-alkene (c)).

The copolymers of the present invention are made up of units which are derived from the monomers carbon monoxide and one or more α-olefinically unsaturated compounds. In the binary copolymers of the present invention, the different monomer units are generally present in a strictly alternating order. In the ternary and higher copolymer systems, the order of carbon monoxide and olefin component is generally likewise strictly alternating, with the crown ether-functionalized alkene monomers being incorporated into the linear copolymer chain essentially randomly in the possible olefin unit positions.

Suitable α-olefinically unsaturated compounds b) are in principle all monomers of this class of compounds which are functionalized by a covalently bonded crown ether unit.

Examples of suitable α-olefinically unsaturated components are the propenyl, 1-butenyl, 1-pentenyl, 1-hexenyl, 1-heptenyl, 1-octenyl, 1-nonenyl, 1-decenyl, 1-dodecenyl, 1-hexadecenyl, 1-octadecenyl or 1-eicosenyl radicals. Preference is given to using compounds b) whose α-olefinically unsaturated component is derived from $C_5$–$C_{18}$-1-alkenyl radicals, particularly preferably $C_7$–$C_{14}$-1-alkenyl radicals.

For the purposes of the present invention, crown ethers in principle include not only crown ethers but also cryptands, podands and coronands as are described, for example, in F. Vögtle, Supramolekulare Chemie, B. G. Teubner, Stuttgart, 1989. In the current context, a crown ether unit is, for example, a macrocyclic polyether compound which has a repeating —O—$(CH_2)_h$-unit (where h=2, 3 or 4). Such compounds include, for example, the cyclic polyethers described in C. J. Pedersen, J. Am. Chem. Soc. 1967, 89, 7017–7036.

Cryptands include essentially all bicyclic polyheteroaromatic macrocycles and in particular all macropolycyclic azapolyethers in which two bridgehead nitrogen atoms are connected by bridges containing one or more oxygen atoms. Suitable cryptands are, inter alia: [2.2.2]-, [2.2.1]-, [2.1.1]- and [1.1.1]-cryptand (for the nomenclature of cryptands, see F. Vögtle, Supramolekulare Chemie, B. G. Teubner, Stuttgart, 1989, p. 47).

Preference is given to crown ether units A containing from 5 to 10 oxygen atoms and cryptand units A containing from 3 to 6 oxygen atoms in which benzene and/or cyclohexane rings can also be integrated into the macrocycle framework, usually via linkages to adjacent ring carbons.

The units A are covalently bonded, generally via a single bond, to the olefinically unsaturated monomer. Bridging structural elements which can be used are, for example, ether, ester, amide or carbamate groups or a carbon/carbon bond. A useful bonding unit is an ester group, where the carboxylic acid radical forming this group preferably comes from the component A and the hydroxyl group comes from the α-olefinically unsaturated monomer unit.

Accordingly, suitable compounds b) can be formally derived from alcohols such as allyl alcohol, but-3-en-1-ol, pent-4-en-1-ol, hex-5-en-1-ol, hept-6-en-1-ol, oct-7-en-1-ol, non-8-en-1-ol, dec-8-en-1-ol, dodec-11-en-1-ol, hexadec-15-en-1-ol, octadec-17-en-1-ol or eicos-19-en-1-ol and crown ethers or cryptands provided with carboxylic acid groups.

A crown ether having a covalently bonded carboxylic acid group is obtained, for example, by acylation of benzo-15-crown-5 (for nomenclature and synthesis see V. Percec, R. Rodenhouse, Macromolecules 1989, 22, 4408) and subsequent oxidation by means of sodium hypobromite (cf. M. Bourgoin, K. H. Wong, J. Y. Hui, J. Smid, J. Am. Chem. Soc. 1975, 97, 3462).

To link the carboxylic acid and alcohol components to form the compound b), recourse can likewise be made to established methods (cf. Vogel's Handbook of Practical Organic Chemistry, 5th Edition, Longman Scientific & Technical, 1989).

Preferred ester-bridged olefinically unsaturated compounds b) have, for example, the formula (I)

$$CH_2=CH(CH_2)_qO(O)C—A \quad (I)$$

where

A = (cyclohexyl-dioxy-G or benzo-dioxy-G structure)

where $$G = —(((CH_2)_kO)_p—(Q—O)_l)_r—(CH_2)_k—,$$

where the substituents and indices have the following meanings:

Q=1,2-cyclohexyl or 1,2-phenyl,
k=independently of one another 2, 3 or 4,
p=1, 2, 3 or 4,
l=0 or 1,
r=1, 2, 3 or 4 and
q=an integer in the range from 4 to 24, in particular from 6 to 16.

Among the compounds mentioned above, particular preference is given to those which have the formula (I)

$$CH_2=CH(CH_2)_qO(O)C—A$$

where q=8 or 9 and
the crown ether functionality is as follows:

A = (cyclohexyl-dioxy-G or benzo-dioxy-G structure)

where $$G=—(CH_2CH_2O)_3—(CH_2CH_2)—.$$

An example of a suitable monomer compound b) for the preparation of the copolymers of the present invention is accordingly 4'-(undec-10-enyl carboxylate)benzo-15-crown-5.

However, suitable compounds b) are not only uniform monomer charges, but also mixtures of compounds in which it is immaterial whether the differences occur in the α-olefinically unsaturated monomer radical or in the crown ether or cryptand component or in both parts at the same time.

The functionalized 1-alkenes b) described can be reacted with carbon monoxide to give the linear, alternating copolymers of the present invention.

In addition, ternary and higher copolymer systems comprising functionalized 1-alkenes b) are likewise obtainable.

In the case of ternary copolymers of the present invention, suitable further monomer components c) are in principle all α-olefinically unsaturated compounds of this class of compounds.

Suitable monomers c) for non-binary copolymers, in particular ternary carbon monoxide copolymers, are, in particular, $C_2$–$C_{24}$-1-alkenes.

Examples which may be mentioned are ethene, propene, 1-butene, 1-pentene, 1-hexene, 1-heptene, 1-octene, 1-nonene, 1-decene, 1-dodecene, 1-hexadecene, 1-octadecene or 1-eicosene. Preference is given to using propene, 1-butene, 1-pentene, 1-hexene 1-heptene, 1-octene, 1-nonene, 1-decene, 1-dodecene, 1-hexadecene and 1-octadecene, in particular propene, 1-hexene, 1-dodecene and 1-octadecene. Among the last-named compounds, particular preference is given to using $C_6$–$C_{12}$-1-alkenes.

Apart from the alkenes mentioned above, conjugated or isolated $C_6$–$C_{20}$-dienes, for example 1,4-hexadiene and 1,5-hexadiene, are also suitable as olefinically unsaturated compounds c).

Preferred terpolymers are derived from carbon monoxide (a)), a compound (b)) which has the formula (I)

$$CH_2=CH(CH_2)_qO(O)C—A \quad (I)$$

where

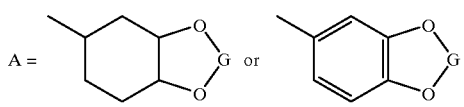

where

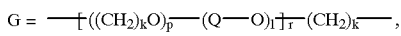

where the substituents and indices have the following meanings:

Q=1,2-cyclohexyl or 1,2-phenyl,
k=independently of one another 2, 3 or 4,
p=1, 2, 3 or 4,
l=0 or 1,
r=1, 2, 3 or 4 and
q=an integer in the range from 4 to 24, in particular from 6 to 16 and a $C_3$–$C_{18}$-1-alkene (c)).

In a particularly preferred embodiment, use is made of terpolymers which can be prepared from carbon monoxide, a compound of the formula (I)

$$CH_2=CH(CH_2)_qO(O)C—A \quad (I),$$

where q=8 or 9
and

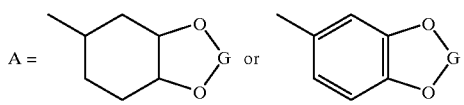

where

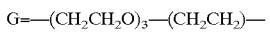

and a $C_6$–$C_{12}$-alkene.

Among the ternary carbon monoxide copolymers, particular mention may be made of the systems based on carbon monoxide/propene/4'-(undec-10-enyl carboxylate)benzo-15-crown-5, carbon monoxide/1-hexene/4'-(undec-10-enyl carboxylate)benzo-15-crown-5, carbon monoxide/1-dodecene/4'-(undec-10-enyl carboxylate)benzo-15-crown-5 and carbon monoxide/1-dodecadecene/4'-(undec-10-enyl carboxylate)benzo-15-crown-5, in particular carbon monoxide/1-hexene/4'-(undec-10-enyl carboxylate)benzo-15-crown-5 and carbon monoxide/1-dodecene/4'-(undec-10-enyl carboxylate)benzo-15-crown-5.

The mean molecular weight $M_w$ (measured by gel permeation chromatography (GPC) at 25° C. using Microstyragel (Waters) as column material and chloroform as solvent against a polystyrene standard) of the carbon monoxide copolymers of the present invention are usually in the range from 5000 to 200,000 g/mol, but copolymers having mean molecular weights up to 300,000 g/mol and even 400,000 g/mol can also be obtained.

While mean molecular weights $M_w$ of greater than 100,000 g/mol can generally be obtained without difficulty when using relatively short-chain monomer components c), eg. propene, the results achieved in the presence of long-chain alkenes such as 1-octadecene are usually lower.

The terpolymers of the present invention are notable for, inter alia, their thermoplastic, elastomeric properties and accordingly have $T_g$ values in the range from 20 to –90° C. For example, carbon monoxide copolymers having a particularly useful thermoplastic, elastomeric property profile are those terpolymers whose component b) is derived from an α-olefin functionalized by benzo-15-crown-5 and whose component c) is derived from a $C_6$–$C_{12}$-alkene.

Terpolymers according to the present invention also include those compounds in which the molar proportion of the component b) in the overall copolymer is 0.01 mol %. However, molar proportions of 5 or 10% or even above can generally be obtained without difficulty.

The proportion of head-to-tail linked units in the terpolymers of the present invention is generally in the range from 1 to 80% and for carbon monoxide copolymers containing, for example, a benzo-15-crown-5 function and $C_3$–$C_{12}$-1-alkenes is usually in the range from 40 to 70%.

The molecular weight distribution $M_w/M_n$ (weight average/number average) of the copolymers of the present invention, measured by gel permeation chromatography (GPC) using a method similar to that described above, is generally from 1.2 to 4, but is preferably less than 2.5.

The molar ratio of carbon monoxide to the sum of the structural units derived from the olefinically unsaturated monomers in the binary and higher carbon monoxide copolymers of the present invention is generally 1:1.

The polymer materials of the present invention have, owing to their impact-modified properties and their biocompatible behavior, many possible uses, eg. in the field of polymer blend technology or in medical technology.

To prepare the linear, thermoplastic, elastomeric copolymers of the present invention, carbon monoxide can be copolymerized with olefinically unsaturated compounds in a virtually alcohol-free or water-free polymerization medium in the presence of a catalyst whose active composition is formed from
A') a metal complex of the formula (II)

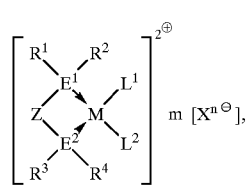

where the bold arrows represent a coordinate bond and the substituents and indices have the following meanings:
M is a metal from group VIIIB of the Periodic Table of the Elements
$E^1$, $E^2$ are each an element from group VA of the Periodic Table of the Elements,
Z is a bridging structural unit comprising one, two, three or four substructural units of elements of groups IVA, VA and VIA of the Periodic Table of the Elements,
$R^1$ to $R^4$ are substituents selected from the group consisting of $C_1$–$C_{20}$-organic and $C_3$–$C_{30}$-organosilicon radicals, where the radicals may contain one or more elements of groups IVA, VA, VIA and VIIA of the Periodic Table of the Elements,
$L^1$, $L^2$ are formally uncharged Lewis base ligands,
X are monovalent or divalent anions,
m, n are 1 or 2,
where m×n=2, and B') is an activator component which contains a hydroxyl group in the molecule and is used, based on M in (II), in an amount of from 0 to 1500 molar equivalents.

As a further process for preparing the linear, thermoplastic, elastomeric copolymers of the present invention, it is possible to copolymerize carbon monoxide with olefinically unsaturated compounds in a virtually alcohol-free or water-free polymerization medium in the presence of a catalyst whose active composition is formed from i) a salt of a metal M of group VIIIB of the Periodic Table of the Elements, ii) one or more compounds selected from the group consisting of protic acids and Lewis acids, iii) a chelating compound of the formula (III)

where the substituents and indices have the following meanings:

$E^1$, $E^2$ are each an element from group VA of the Periodic Table of the Elements, Z is a bridging structural unit comprising one, two, three or four substructural units of elements of groups IVA, VA and VIA of the Periodic Table of the Elements, $R^1$ to $R^4$ are substituents selected from the group consisting of $C_1$–$C_{20}$-organic and $C_3$–$C_{30}$-organosilicon radicals, where the radicals may contain one or more elements from groups IVA, VA, VIA and VIIA of the Periodic Table of the Elements, d) an activator component B') which contains a hydroxyl group in the molecule and is used, based on M in (II), in an amount of from 0 to 1500 molar equivalents.

The polymerizations for preparing the carbon monoxide copolymers of the present invention can be carried out either batchwise or continuously in the presence of a polymerization catalyst comprising A'), or i), ii), iii) and possibly B') or iv).

Suitable polymerization catalysts are transition metal compounds of group VIIIB of the Periodic Table of the Elements which are in the form of defined metal complexes (II) or can be formed in situ from a metal salt i) of a metal of group VIIIB of the Periodic Table of the Elements, protic and/or Lewis acids ii) and a chelating compound iii) of the formula (III). If desired, activators B') or iv) can be added to the metal compounds.

Suitable metals M are the metals of group VIIIB of the Periodic Table of the Elements, ie. iron, cobalt and nickel and especially the platinum metals ruthenium, rhodium, osmium, iridium, platinum and very particularly palladium. In the metal complexes, the metals nickel, palladium and platinum generally formally bear two positive charges, the metals cobalt, rhodium and iridium generally formally bear one positive charge and the metals iron, ruthenium and osmium are generally formally uncharged.

Suitable elements $E^1$ and $E^2$ in the chelating ligand, hereinafter also referred to as chelating compound (III), are the elements of main group V of the Periodic Table of the Elements (group VA), ie. nitrogen, phosphorus, arsenic, antimony or bismuth. Particularly suitable elements are nitrogen and phosphorus, in particular phosphorus. The chelating ligand or the chelating compound (III) can contain different elements $E^1$ and $E^2$, for example nitrogen and phosphorus, but it preferably contains identical elements $E^1$ and $E^2$ and in particular $E^1$ and $E^2$ are phosphorus.

The bridging structural unit Z is a group of atoms which connects the two elements $E^1$ and $E^2$ to one another. Substructural units comprising one atom or a plurality of atoms connected to one another from group IVA, VA or VIA of the Periodic Table of the Elements usually form the bridge between $E^1$ and $E^2$. Possible free valences of these bridge atoms can be satisfied in various ways, for example by bonding to hydrogen or elements of group IVA, VA, VIA or VIIA of the Periodic Table of the Elements. These substituents can form ring structures with one another or with the bridge atom.

Well suited bridging structural units Z are those comprising one, two, three or four elements from group IVA of the Periodic Table of the Elements, for example methylene (—$CH_2$—), 1,2-ethylene (—$CH_2$—$CH_2$—), 1,3-propylene (—$CH_2$—$CH_2$—$CH_2$—), 1,4-butylene, 1,3-disilapropylene (—$R^5R^6Si$—$CH_2$—$SiR^5R^6$—, where $R^5$, $R^6$ are $C_1$–$C_{10}$-alkyl, $C_6$–$C_{10}$-aryl), ethylidene ($CH_3(H)C$=), 2-propylidene (($CH_3)_2C$=), diphenylmethylene (($C_6H_5)_2C$=) or ortho-phenylene.

Particularly suitable bridging structural units are 1,2-ethylene, 1,3-propylene and 1,4-butylene.

Suitable organic radicals $R^1$ to $R^4$ are, independently of one another, aliphatic, cycloaliphatic and aromatic radicals having from 1 to 20 carbon atoms, for example the methyl, ethyl, 1-propyl, 1-butyl, 1-pentyl, 1-hexyl and 1-octyl groups as well as their structural analogues. Linear arylalkyl groups having from 1 to 10 carbon atoms in the alkyl radical and from 6 to 20 carbon atoms in the aryl radical, for example benzyl, are also suitable. Further radicals $R^1$ to $R^4$ which may be mentioned are aryl radicals such as tolyl, anisyl, preferably ortho-anisyl, xylyl and other substituted phenyl groups, in particular phenyl.

Possible cycloaliphatic radicals are $C_3$–$C_{10}$-monocyclic systems such as cyclopropyl, cyclobutyl, cyclopentyl and cyclohexyl, particularly preferably cyclohexyl.

Suitable branched aliphatic radicals are $C_3$–$C_{20}$—, preferably $C_3$–$C_{12}$-alkyl radicals such as i-propyl, i-butyl, s-butyl, neopentyl and t-butyl.

Particularly suitable branched aliphatic radicals are t-butyl, i-propyl and s-butyl.

Alkyl groups having branching located further out are also well suited as substituents $R^1$ to $R^4$, for example i-butyl, 3-methylbut-2-yl and 4-methylpentyl.

The substituents $R^1$ to $R^4$ can also, independently of one another, contain atoms from group IVA, VA, VIA or VIIA of the Periodic Table of the Elements, for example halogen, oxygen, sulfur, nitrogen or silicon, for example the bis (trimethylsilyl)methyl group. Functional groups which are inert under the polymerization conditions are also possibilities in this context.

Preferred heterosubstituents $R^1$ to $R^4$ are $C_3$–$C_{30}$-organosilicon radicals, ie. tetravalent silicon atoms which are bonded to $E^1$ or $E^2$ and whose remaining valences bear three organic radicals such as alkyl and/or aryl radicals, where the total number of carbon atoms in these three radicals bonded to silicon is in the range from three to thirty. Examples which may be mentioned are the trimethylsilyl, t-butyldimethylsilyl and triphenylsilyl groups, in particular the trimethylsilyl group.

The chelating ligand or chelating compound (III) used is preferably 1,2-bis(diphenylphosphino)ethane, 1,3-bis (diphenylphosphino)propane or 1,4-bis(diphenylphosphino) butane.

Very particularly preferred compounds as chelating ligand or chelating compound (III) are 1,3-bis(diphenylphosphino) propane and 1,4-bis(diphenylphosphino)butane.

Suitable formally uncharged ligands $L^1$, $L^2$ are Lewis bases in general, ie. compounds, preferably organic compounds, having at least one free electron pair or water.

Well suited ligands are Lewis bases whose free electron pair or pairs is/are located on a nitrogen or oxygen atom, ie. nitriles, R—CN, ketones, ethers or preferably water.

Suitable Lewis bases which may be mentioned are $C_1$–$C_{10}$-nitriles such as acetonitrile, propionitrile or benzonitrile, or $C_3$–$C_{10}$-ketones such as acetone or acetylacetone or else $C_2$–$C_{10}$-ethers such as dimethyl ether, diethyl ether or tetrahydrofuran.

Ligands $L^1$, $L^2$ in (II) which are particularly suitable for catalysts which need no activator B') or iv) are those of the formula (IV)

$$T\text{—OH} \tag{IV}$$

where T is hydrogen or a $C_1$–$C_{15}$-organic radical bearing a Lewis base group. Well suited $C_1$–$C_{15}$-organic radicals T are, for example, linear or cyclic $\text{—(CH}_2\text{)}_n$ units, where n is from 1 to 10, ie. methylene, 1,2-ethylene, 1,3-propylene, 1,4-butylene, 1,5-pentylene, 1,6-hexylene, 1,7-heptylene, 1,8-octylene, 1,9-nonylene or 1,10-decylene.

Suitable Lewis base groups are ether, ester, ketone, amine, phosphine and in particular nitrile (—C≡N) or tertiary amine.

Examples of well suited compounds T—OH are water and α,ω-hydroxynitriles such as NC–$(CH_2)_n$–OH where n=1–10 and (2-hydroxymethyl)tetrahydrofuran, as well as (2-hydroxymethyl)(N-organo)pyrrolidines (IVa) and (2-hydroxymethyl)(N-organo)piperidines (IVb)

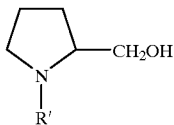

(IVa)

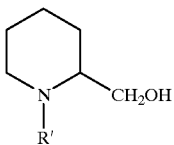

(IVb)

where R' is $C_1$–$C_{10}$-alkyl or $C_3$–$C_{10}$-cycloalkyl, for example methyl, ethyl, n-propyl, i-propyl, n-butyl, i-butyl, s-butyl, t-butyl, cyclopentyl and cyclohexyl. R' can also be $C_6$–$C_{10}$-aryl, for example phenyl or naphthyl.

In general, the ligands T—OH are, with the exception of water, bonded to the metal M in (II) via the above-defined Lewis base group.

The choice of the anions X is generally not critical. Examples of suitable anions X in (II) are perchlorate, sulfate, phosphate, nitrate and carboxylates such as acetate, trifluoroacetate, trichloroacetate, propionate, oxalate, citrate and benzoate, and also conjugated anions of organosulfonic acids, for example methylsulfonate, trifluoromethylsulfonate and p-toluenesulfonate, also tetrafluoroborate, tetraphenylborate, tetrakis(pentafluorophenyl)borate, hexafluorophosphate, hexafluoroarsenate and hexafluoroantimonate. Preference is given to using perchlorate, trifluoroacetate, sulfonates such as methylsulfonate, trifluoromethylsulfonate and p-toluenesulfonate, tetrafluoroborate or hexafluorophosphate and in particular trifluoroacetate, perchlorate or p-toluenesulfonate as anion X.

Particularly well suited metal complexes (II) which may be mentioned are (1,3-bis(diphenylphosphino)propane)bis(acetonitrile)palladium bis(tetrafluoroborate) (=[Pd(dppp)(NCCH$_3$)$_2$](BF$_4$)$_2$, dppp=1,3-bis(diphenylphosphino)propane), (1,3-bis(diphenylphosphino)propane) diaquopalladium bis(tetrafluoroborate), (1,3-bis(diphenylphosphino)propane)bis(3-hydroxypropionitrile) palladium bis(tetrafluoroborate), (1,4-bis(diphenylphosphino)butane)bis(acetonitrile)palladium bis(tetrafluoroborate) and (1,4-bis(diphenylphosphino)butane) diaquopalladium bis(tetrafluoroborate).

The metal complexes of the formula (II) are generally prepared by literature methods, as described in Makromol. Chem. 1993, 194, p. 2579. Tetrakis(ligand)metal complexes such as tetrakis(acetonitrile)palladium bis(tetrafluoroborate) can usually be reacted with the chelating compounds (III) and the ligands $L^1$, $L^2$ or TOH to give the metal complexes (II). A preferred method of preparing aquo complexes (II) is reacting the (chelating phosphine)(acetonitrile)metal complexes with water. The reaction is generally carried out in a solvent, for example dichloromethane, acetonitrile or water, at from −78 to 40° C.

In the in situ generation of the polymerization catalysts, the metals M are usually used in divalent form as their salts and are brought into contact with the chelating compound iii) of the formula (III) and the acids ii). This can occur before contacting the catalytically active composition obtainable in this way with the monomers and, if desired, a further activator iv), generally outside the polymerization reactor. However, the reaction of the individual components metal salt i), chelating compound iii) of the formula (III), acid ii) and any activator component iv) used can also be carried out in the polymerization reactor, in the presence of the monomers.

Suitable salts of usually divalent metals M are halides, sulfates, phosphates, nitrates and carboxylates such as acetates, propionates, oxalates, citrates and benzoates, and also sulfonic acid salts such as methylsulfonates, trifluoromethylsulfonates and p-toluenesulfonates. Preference is given to using carboxylates, sulfonic acid derivatives and in particular acetates.

Particularly suitable catalyst components i) are palladium dicarboxylates, preferably palladium diacetate, palladium dipropionate, palladium bis(trifluoroacetate) and palladium oxalate, and also palladium sulfonates, preferably palladium bis(trifluoromethanesulfonate), palladium bis(methanesulfonate) and palladium bis(p-toluenesulfonate). Particular preference is given to using palladium diacetate.

As catalysts constituents ii), it is possible to use Lewis and protic acids and mixtures thereof.

Suitable protic acids ii) are strong mineral acids such as sulfuric acid and perchloric acid, and also strong organic acids such as trichloroacetic and trifluoroacetic acids, and also the sulfonic acids methanesulfonic acid, p-toluenesulfonic acid and benzenesulfonic acid, ie. in each case acids which preferably have a $pK_a$ of less than 3.

The acidic salts of strong acids and weak bases, for example ammonium salts of the abovementioned acids, are also suitable.

Examples of suitable Lewis acids are halides of the elements of group IIIA of the Periodic Table of the Elements, for example boron trifluoride, boron trichloride, aluminum trifluoride and aluminum trichloride, halides of the elements of group VA of the Periodic Table of the Elements, eg. phosphorus pentafluoride and antimony pentafluoride, and also halides of the metals of transition group IVB of the Periodic Table of the Elements, for example titanium tetrachloride and zirconium tetrachloride. Further suitable Lewis acids are organically substituted Lewis acids, for example tris(pentafluorophenyl)borane.

As Lewis acids, preference is given to using boron trifluoride, antimony pentafluoride or tris(pentafluorophenyl)borane.

Particularly preferred components ii) are those which possess a weakly coordinating conjugated anion, ie. an anion which forms only a weak bond to the central metal of the complex, for example tetrafluoroborate, hexafluorophosphate, perchlorate, trifluoroacetate, trifluoromethylsulfonate, p-tosylate and borates such as catecholatoborate and tetraarylborate, where particularly suitable aryl groups are 2,5-dimethylphenyl, 2,5-bis (trifluoromethyl)phenyl and pentafluorophenyl.

Otherwise, suitable catalyst components i) and ii) are those which are generally known from EP-A 501 576 and 516 238 for systems containing bisphosphines.

As component c), the catalyst systems comprise a chelating compound $R^1R^2E^1$—Z—$E^2R^3R^4$ (III), which has already been described in the discussion of the metal complexes (II).

The ratio of the catalyst constituents i), ii) and iii) to one another is generally selected such that the molar ratio of the metal compound i) to the acid ii) is from 0.01:1 to 100:1, preferably from 0.1:1 to 1:1, and the molar ratio of the metal compound i) to the component iii) is from 0.01:1 to 10:1, preferably from 0.1:1 to 2:1.

The activator component B') or iv) is generally a chemical compound which contains at least one hydroxyl group in the molecule. These include, in particular, $C_1$-$C_{10}$-alcohols such as methanol, ethanol, n-propanol, i-propanol, n-butanol, i-butanol, s-butanol, t-butanol, n-hexanol, n-octanol, n-decanol and cyclohexanol, phenol or water. Preference is given to using methanol and/or water as activator component B') or iv).

The molar ratio of activator component B') or iv) to metal M is in the range from 0 to 1500, preferably in the range from 0 to 1300. It has found to be advantageous not to exceed the maximum ratio in the polymerization reaction, since otherwise the mean molecular weights $M_w$ of the carbon monoxide copolymers formed can be too low.

The addition of the activator B') or iv) becomes superfluous only when the Lewis base ligands $L^1$, $L^2$ present in the catalyst are ones which contain a hydroxyl group in the molecule and have been defined more precisely above by the formula T—OH (IV).

Particularly suitable reaction parameters for preparing the linear, thermoplastic, elastomeric copolymers of carbon monoxide and olefinically unsaturated compounds have been found to be pressures of from 100 to 500,000 kPa, preferably from 500 to 350,000 kPa and in particular from 1000 to 10,000 kPa, and temperatures of from −50 to 400° C., preferably from 10 to 250° C. and in particular from 20 to 100° C.

The polymerization reactions can be carried out in the gas phase in a fluidized bed or stirred, in suspension, in liquid or supercritical monomers and in solvents which are inert under the polymerization conditions.

The polymerization reactions can be carried out in a virtually alcohol-free or water-free polymerization medium. This means that no alcohol or water apart from perhaps the activator component B') or iv) is added to the reaction mixture comprising monomers, catalyst and, if desired, inert solvent or suspension medium.

Suitable inert solvents and suspension media are those which contain no hydroxyl group in the molecule, ie. ethers such as diethyl ether, tetrahydrofuran, aromatic solvent such as benzene, toluene, ethylbenzene, chlorobenzene, aliphatic hydrocarbons such as i-butane or chlorinated aliphatic hydrocarbons such as dichloromethane, 1,1,1-trichloromethane or mixtures of these.

A polymerization method which has been found to be particularly well suited is to place the catalyst in an inert solvent, if desired subsequently add the activator component B') or iv) and subsequently add the monomers and to carry out the polymerization at from 20 to 100° C. and a pressure in the range from 1000 to 10,000 kPa.

The carbon monoxide copolymers of the present invention can be processed by means of injection molding, blow molding, spinning, rotation molding, extrusion or spin coating. It is also possible to coat metallic, ceramic and other surfaces, eg. those of polymer materials.

The carbon monoxide copolymers of the present invention are suitable for producing fibers, films, moldings and coatings. Furthermore, they are suitable for producing ion-selective membranes.

As a result of the above-described controlled incorporation of crown ether functions into the carbon monoxide copolymer framework and the possibility of influencing the thermoplastic, elastomeric behavior of these copolymers by means of the molecular weight and/or the incorporation of long-chain olefin building blocks, it is possible to produce films which are particularly suitable as ion-selective membranes. These membranes can be used, inter alia, as a constitutent of compact analytical devices such as ion-selective electrodes (cf. J. Moody, B. B. Saad, J. D. R. Thomas, Selective Electrode Rev. 1988, 10, 71) or in chemically modified field effect transistors (CHEMFETs for short) (see also D. N. Reinhoudt, J. F. J. Engbersen, Z. Brzózka, H. N. van den Vlekkert, G. W. N. Honig, H. A. J. Holterman, U. H. Verkerk, Anal. Chem. 1994, 66, 3618). The membranes of the present invention are particularly notable for not requiring any plasticizer and for the activation energy for the transport of ions being minimized as a result of the presence of polar CO groups in the polymer. At the same time, however, the hydrophobic surface character is retained, which substantially suppresses or completely eliminates the process of fouling in the aqueous phase.

Accordingly, membranes based on the carbon monoxide copolymers of the present invention open out a simple route to, for example, sensor components which have a long life and can be produced on a large scale without difficulty.

The invention is illustrated by the following examples.

EXAMPLES

I. Measurement methods and apparatus

The molecular weights $M_w$ and the molecular weight distributions $M_w/M_n$ were determined by GPC in $CHCl_3$ using a Waters 590 HPLC pump, Waters Microstyragel columns having pore sizes of $10^5$, $10^4$ and $10^3$ Å, a Waters 410 differential refractometer and a Waters 486 UV detector.

$^1$H-NMR and $^{13}$C-NMR measurements were carried out using a Bruker AC 200 spectrometer.

The DSC data were determined using a Perkin Elmer DSC 7 instrument equipped with a Perkin Elmer TAC 7/DX thermocontroller; cyclohexane, indium and gallium were used for calibration.

Melting points were determined on a Mettler FP82HT hotplate and a Mettler FP90 processor using a Zeiss Axioskop Pol microscope.

IR spectra were recorded on a Bruker IFS 66V spectrometer. The samples for measurement were produced by applying a thin film to KBr plates from a dichloromethane solution.

The catalyst used was [Pd(dppp)(NCCH$_3$)$_2$] (BF$_4$)$_2$, prepared from [Pd(NCCH$_3$)$_4$](BF$_4$)$_2$ (Aldrich) and 1,3-bis (diphenylphosphino)propane (=dppp) (Strem Chemicals) as described by F. Y. Xu, A. X. Zhao, J. C. W. Chien, Makromol. Chem. 1993, 194, 2597.

Toluene, dichloromethane and triethylamine were distilled over sodium, benzophenone and calcium hydride or KOH respectively before use. Methanol was purified by distillation over magnesium wire.

II. Preparation of 4'-(undec-10-enylcarboxylate)benzo-15-crown-5 (V) (component b))

A mixture of 4'-benzo-15-crown-5-carboxylic acid (10 g, 32 mmol), obtainable from benzo-15-crown-5 by the method of M. Bourgoin, K. H. Wong, J. Y. Hui, J. Smid, J. Am. Chem. Soc. 1975, 97, 3462, and thionyl chloride (50 ml, 293 mmol) was refluxed for 6 hours, excess thionyl chloride was distilled off and the residue was dissolved in dichloromethane (40 ml). Undec-10-en-1-ol (6.54 g, 38.4 mmol), dissolved in dichloromethane (20 ml), was admixed with triethylamine (6.8 ml, 48 mmol) in dichloromethane (20 ml) and the mixture was added dropwise at room temperature to the reaction mixture. After 12 hours under reflux, the reaction was stopped by cooling and washing three times with water.

The organic phase was separated off, dried over $MgSO_4$, the organic solvent was removed and the resulting crude product was chromatographed on silica gel using first dichloromethane and subsequently a 95/5 (v/v) mixture of dichloromethane and methanol (yield: 11.5 g), m.p.: 42–43° C.

IR (KBr) 1712 $cm^{-1}$ (C=O). $^1$H NMR ($CDCl_3$): δ=1.25 (m, —(C$\underline{H}_2$)$_6$—, 12H), 1.70 (m, —C$\underline{H}_2$CH$_2$O$_2$C—, 2H), 2.0 (m, CH$_2$=CHC$\underline{H}_2$—, 2H) 3.70 (s, —OCH$_2$CH$_2$OCH$_2$CH$_2$O—, 8H), 3.85 (d, ArOCH$_2$C$\underline{H}_2$O—, 4H), 4.10 (d, ArOC$\underline{H}_2$CH$_2$O—, 4H), 4.20 (t, —C$\underline{H}_2$O$_2$CAr, 2H), 4.85 (m, CH=C$\underline{H}_2$—, 2H), 5.70 (m, C$\underline{H}$=CH$_2$—, 1H), 6.80 (d, ArH, 1H), 7.45 (s, ArH, 1H), 7.60 (d, ArH, 1H). $^{13}$C NMR ($CDCl_3$): δ=25.84, 28.57, 28.71, 28.89, 29.20 and 29.26 (—(C$\underline{H}_2$)$_7$—), 33.59 (CH$_2$=CHC$\underline{H}_2$—), 64.73 (—C$\underline{H}_2$O$_2$CAr), 68.46, 68.89, 69.10, 69.24, 70.15, 70.25 and 70.99 (crown ether carbons), 111.92, 114.49, 123.05, 123.66, 148.29 and 152.95 (aromat. C), 113.96 (C$\underline{H}_2$=CH—), 138,93 (CH=C$\underline{H}_2$—), 166.15 (C=O).

III. Terpolymerization of 4'-(undec-10-enyl carboxylate)benzo-15-crown-5 (V) and carbon monoxide with propene (C3), 1-hexene (C6), 1-dodecene (C12) and 1-octadecene (C18)

General Procedure:

The polymerizations were carried in 25 ml of dichloromethane in 50 or 100 ml steel autoclaves by stirring at room temperature under a CO pressure of 6.1×10$^6$ Pa. The amount of the activator (methanol) added in each case, the amounts of α-olefin and catalyst used and the reaction conditions are shown in Table 1.

The polymerization was stopped by venting the autoclave and adding of an excess of methanol. Subsequently, the solvent was removed, the residue was taken up in dichloromethane and freed of catalyst residues by means of a short silica gel column. The last traces of unreacted 4'-(undec-10-enylcarboxylate)benzo-15-crown-5 and α-olefin (for C3, C6, C12) were removed by (repeated) precipitation of the products in a dichloromethane solution by addition of methanol. Removal of the solvent under reduced pressure gave the desired terpolymer. Unreacted 1-octadecene was removed by chromatography on silica gel (0.063–0.100 mm) using dichloromethane and a 90/10 (v/v) mixture of dichloromethane and methanol. The product properties of C3, C6, C12, C18 are shown in section IV. and also Table 2.

IV. Spectroscopic data

C3: $^1$H NMR ($CDCl_3$): δ=1.05 (broad, —C$\underline{H}_3$, 3H), 2.20–2.50 (broad, —C$\underline{H}$—, 1H), 2.70–3.20 (broad, —C$\underline{H}_2$—, 2H), 3.70 (s, —OCH$_2$CH$_2$OCH$_2$CH$_2$O—, 8H), 3.85 (d, ArOCH$_2$C$\underline{H}_2$O—, 4H), 4.10 (d, ArOC$\underline{H}_2$CH$_2$O—, 4H), 4.20 (t, —C$\underline{H}_2$O$_2$CAr, 2H), 6.80 (d, ArH, 1H), 7.45 (s, ArH, 1H), 7.60 (d, ArH, 1H). $^{13}$C NMR ($CDCl_3$): δ=16.20 (—C$\underline{H}_3$), 39.86 (—C$\underline{H}_2$— framework), 44.46 (—C$\underline{H}$— framework), 207.5 (C=O framework, tail—tail linkage), 212.0 (C=O framework, head-tail linkage), 215.6 (C=O framework, head—head linkage).

C6: $^1$H NMR ($CDCl_3$): δ=0.85 (t, —C$\underline{H}_3$, 3H), 1.00–1.80 (broad, —(C$\underline{H}_2$)$_3$—, 6H), 2.20–2.60 (broad, —C$\underline{H}$—, 1H), 2.70–3.20 (broad, —CH$_2$—, 2H), 3.70 (s, —OCH$_2$CH$_2$OCH$_2$CH$_2$O—, 8H), 3.85 (d, ArOCH$_2$C$\underline{H}_2$O—, 4H), 4.10 (d, ArOC$\underline{H}_2$CH$_2$O—, 4H), 4.20 (t, —C$\underline{H}_2$O$_2$CAr, 2H), 6.80 (d, ArH, 1H), 7.45 (s, ArH, 1H), 7.60 (d, ArH, 1H). $^{13}$C NMR ($CDCl_3$): δ=13.50 (—C$\underline{H}_3$), 22.30 (—C$\underline{H}_2$CH$_3$), 23.19, 25.61, 26.38, 28.84, 30.54 and 32.29 (—(C$\underline{H}_2$)$_n$—), 41–42 (—C$\underline{H}$— framework), 43–45 (—C$\underline{H}_2$— framework), 68.20, 68.64, 68.86, 69.00, 69.91, 70.00 and 70.74 (crown ether carbons), 111.65, 114.18, 122.74, 123.44, 148.06 and 152.73 (aromat. C), 165.83 (C=O ester), 208–211 (C=O framework, tail—tail linkage), 212–214 (C=O framework, head-tail linkage), 214–216 (C=O framework, head—head linkage).

C12: $^1$H NMR ($CDCl_3$): δ=0.85 (t, —C$\underline{H}_3$, 3H), 1.0–1.80 (broad, —(C$\underline{H}_2$)$_9$—, 18H), 2.20–2.70 (broad, —C$\underline{H}$—, 1H), 2.70–3.20 (broad, —C$\underline{H}_2$—, 2H), 3.70 (s, —OCH$_2$CH$_2$OCH$_2$CH$_2$O—, 8H), 3.85 (d, ArOCH$_2$C$\underline{H}_2$O—, 4H), 4.10 (d, ArOC$\underline{H}_2$CH$_2$O—, 4H), 4.20 (t, —C$\underline{H}_2$O$_2$CAr, 2H), 6.80 (d, ArH, 1H), 7.45 (s, ArH, 1H), 7.60 (d, ArH, 1H). $^{13}$C NMR ($CDCl_3$): δ=13.70 (—C$\underline{H}_3$), 22.30 (—C$\underline{H}_2$CH$_3$), 23.27, 26.60, 28.98, 29.23, 30.91 and 31.54 (—(C$\underline{H}_2$)$_n$—), 41–42 (—C$\underline{H}$— framework), 43–45 (—C$\underline{H}_2$— framework), 68.17, 68.58, 68.86, 69.91 and 70.74 (crown ether carbons), 111.52, 114.14, 122.73, 123.37, 148.05 and 152.70 (aromat. C), 165.60 (C=O ester), 207–209 (C=O framework, tail—tail linkage), 210–212 (C=O framework, head-tail linkage), 212–215 (C=O framework, head—head linkage).

C18: $^1$H NMR ($CDCl_3$) δ=0.85 (t, —C$\underline{H}_3$, 3H), 1.0–1.80 (broad, —(C$\underline{H}_2$)$_{15}$—, 30 H), 2.20–2.70 (broad, —C$\underline{H}$—, 1H), 2.70–3.20 (broad, —C$\underline{H}_2$—, 2H), 3.70 (s, —OCH$_2$CH$_2$OCH$_2$CH$_2$O—, 8H), 3.85 (d, ArOCH$_2$C$\underline{H}_2$O—, 4H), 4.10 (d, ArOC$\underline{H}_2$CH$_2$O—, 4H), 4.20 (t, —C$\underline{H}_2$O$_2$CAr, 2H), 6.80 (d, ArH, 1H), 7.45 (s, ArH, 1H), 7.60 (d, ArH, 1H). $^{13}$C NMR ($CDCl_3$): δ=13.76 (—C$\underline{H}_3$), 22.36 (—C$\underline{H}_2$CH$_3$), 23.42, 24.30, 25.71, 26.68, 28.44, 29.08, 29.41, 31.03 and 31.62 (—(C$\underline{H}_2$)$_n$—), 41–42 (—C$\underline{H}$— framework), 43–45 (—C$\underline{H}_2$— framework), 68.10, 68.52, 68.84, 69.83 and 70.60 (crown ether carbons), 111.57, 114.14, 122.86, 123.47, 147.95 and 152.56 (aromat. C), 165.60 (C=O ester), 207–209 (C=O framework, tail—tail linkage), 210–212 (C=O framework, head-tail linkage), 212–215 (C=O framework, head—head linkage).

TABLE 1

Polymerization conditions

| Polymer | α-Olefin, g | (mmol) | V, g | (mmol) | Methanol/Pd[a] | $t_{pol}$[b], h | $CO_{consump}$[c], Pax10$^{-5}$ | Yield[d], g |
|---|---|---|---|---|---|---|---|---|
| C3 | 25 | (594) | 0.3 | (0.7) | 1100 | 40 | 25[e] | 2.5 |
| C6 | 1.3 | (15.9) | 0.6 | (1.4) | 1100 | 45 | 20[f] | 0.7 |
| C12 | 3.8 | (22.6) | 0.5 | (1.1) | 300 | 64 | 20[f] | 1.2 |
| C18 | 4.7 | (18.8) | 0.6 | (1.2) | 300 | 43 | 18[f] | 0.5 |

[a]Molar ratio of activator (methanol) to palladium
[b]Polymerization time.
[c]Carbon monoxide consumption. The initial pressure was 6 × 10$^6$ Pa in all cases.
[d]Yield of product isolated after precipitation and chromatography.
[e]100 ml autoclave.
[f]50 ml autoclave.

TABLE 2

Terpolymer properties

| Polymer | $M_w$[a] g/mol | $M_w/M_n$[a] | (V) (mol %)[b] $^1$H NMR | (V) (mol %)[b] $^{13}$C NMR | H-T[c] mol % | $v_{C=O}$[d] cm$^{-1}$ | $T_g$[e] °C | $T_m$[e] °C |
|---|---|---|---|---|---|---|---|---|
| C3 | 131200 | 1.8 | ~0.2 | —[h] | 57 | 1706 | 19 | 108 |
| C6 | 12800 | 1.5 | 5.4 | 4.7 | 60 | 1708 | -18 | —[g] |
| C12 | 11000 | 2.0 | 4.4 | 4.3 | 52 | 1708 | -76 | —[g] |
| C18 | 5300 | 1.8 | 9.6 | 9.0 | 4.9 | 1710 | —[f] | 17 |

[a]$M_w$ ($M_w/M_n$) determined by means of GPC in chloroform (against a polystyrene standard).
[b](V): Determined by means of the proportion of benzo-15-crown-5 units (mol %).
[c]Head-tail units: Regioregularity determined by means of the head-tail sequences using $^{13}$C NMR.
[d]C=O Infrared absorption bands.
[e]Determined from the second run (10K/min) using the tangent method (DSC).
[f]$T_g$ not able to be determined.
[g]$T_m$ not able to be determined.
[h]No signal detectable by means of $^{13}$C NMR.

We claim:

1. A linear, alternating α-olefin-CO copolymer obtained by polymerization of a monomer mixture comprising a) carbon monoxide, b) 1-alkenes which are functionalized by a covalently bonded crown ether unit or cryptand unit A containing at least 5 heteroatoms selected from the group consisting of nitrogen, oxygen, sulfur and selenium in the polyheteroatom framework, and, if desired, c) $C_2$–$C_{24}$-1-alkenes.

2. A linear, alternating α-olefin-CO copolymer as claimed in claim 1, wherein a) is carbon monoxide, b) is a 1-alkene which is functionalized by a covalently bonded crown ether unit A containing from 5 to 10 oxygen atoms, and c) is a $C_2$–$C_{20}$-1-alkene.

3. A linear, alternating α-olefin-CO copolymer as claimed in claim 1, wherein a) is carbon monoxide, b) is a compound of the formula (I)

where

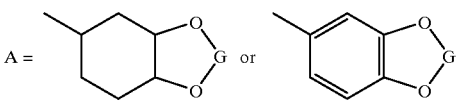

where

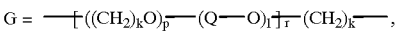

where the substituents and indices have the following meanings:

Q=1,2-cyclohexyl or 1,2-phenyl,
k=independently of one another 2, 3 or 4,
p=1, 2, 3 or 4,
l=0 or 1,
r=1, 2, 3 or 4 and
q=an integer in the range from 4 to 24 and c) is a $C_3$–$C_{18}$-1-alkene.

4. A linear, alternating α-olefin-CO-copolymer as claimed in claim 1, wherein a) is carbon monoxide, b) is a compound of the formula (I)

where q=8 or 9 and

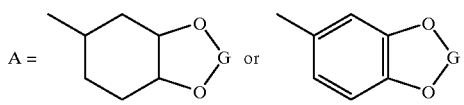

where
G=—(CH$_2$CH$_2$O)$_3$—(CH$_2$CH$_2$)—
and c) is a C$_6$–C$_{12}$-1-alkene.

5. A process for preparing linear, alternating α-olefin-CO copolymers as claimed in claim 1, which comprises carrying out the copolymerization of carbon monoxide a) with the olefinic monomers b) and, if desired, c) in a virtually alcohol-free or water-free polymerization medium in the presence of a catalyst whose active composition is formed from A') a metal complex of the formula (II)

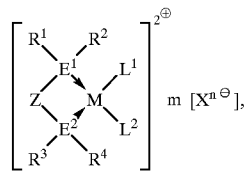 (II)

where the substituents and indices have the following meanings:

M is a metal from group VIIIB of the Periodic Table of the Elements

E$^1$, E$^2$ are each an element from group VA of the Periodic Table of the Elements, Z is a bridging structural unit comprising one, two, three or four substructural units of elements of groups IVA, VA and VIA of the Periodic Table of the Elements, R$^1$ to R$^4$ are substituents selected from the group consisting of C$_1$–C$_{20}$-organic and C$_3$–C$_{30}$-organosilicon radicals, where the radicals may contain one or more elements of groups IVA, VA, VIA and VIIA of the Periodic Table of the Elements, L$^1$, L$^2$ are formally uncharged Lewis base ligands, X are monovalent or divalent anions, m, n are 1 or 2, where m×n=2, and B') is an activator component which contains a hydroxyl group in the molecule and is used, based on M in (II), in an amount of from 0 to 1500 molar equivalents.

6. A process for preparing linear, alternating α-olefin-CO copolymers as claimed in claim 1, wherein the copolymerization in carried out in the presence of a catalyst whose active composition is formed from i) a salt of a metal M of group VIIIB of the Periodic Table of the Elements, ii) one or more compounds selected from the group consisting of protic acids and Lewis acids, iii) a chelating compound of the formula (III)

 (III), where the substituents and indices have the following meanings:

E$^1$, E$^2$ are each an element from group VA of the Periodic Table of the Elements, Z is a bridging structural unit comprising one, two, three or four substructural units of elements of groups IVA, VA and VIA of the Periodic Table of the Elements, R$^1$ to R$^4$ are substituents selected from the group consisting of C$_1$–C$_{20}$-organic and C$_3$–C$_{30}$-organosilicon radicals, where the radicals may contain one or more elements from groups IVA, VA, VIA and VIIA of the Periodic Table of the Elements, iv) an activator component B') which contains a hydroxyl group in the molecule and is used, based on M in (II), in an amount of from 0 to 1500 molar equivalents.

7. A process for producing fibers, films, moldings, ion-selective membranes and coatings, in which linear, alternating α-olefin-CO copolymers as claimed in claim 1.

8. A fiber, film, molding or coating comprising a linear, alternating α-olefin-CO copolymer as claimed in claim 1.

9. An ion-selective membrane comprising an α-olefin-CO copolymer as claimed in claim 1.

10. An ion-selective electrode or a chemically modified field effect transistor comprising as significant constituent an ion-selective membrane as claimed in claim 9.

* * * * *